(12) United States Patent
Nickisch et al.

(10) Patent No.: US 9,096,641 B2
(45) Date of Patent: Aug. 4, 2015

(54) IMIDAZOLYL PROGESTERONE ANTAGONISTS

(71) Applicants: Klaus Nickisch, Berlin (DE); Walter Elger, Berlin (DE); Bindu Santhamma, San Antonio, TX (US)

(72) Inventors: Klaus Nickisch, Berlin (DE); Walter Elger, Berlin (DE); Bindu Santhamma, San Antonio, TX (US)

(73) Assignee: Evestra, Inc., San Antonio, TX (US)

( * ) Notice: Subject to any disclaimer, the term of this patent is extended or adjusted under 35 U.S.C. 154(b) by 17 days.

(21) Appl. No.: 13/910,273

(22) Filed: Jun. 5, 2013

(65) Prior Publication Data

US 2014/0364600 A1 Dec. 11, 2014

(51) Int. Cl.
*C07J 21/00* (2006.01)
*C07J 43/00* (2006.01)

(52) U.S. Cl.
CPC ............... *C07J 43/003* (2013.01); *C07J 21/00* (2013.01)

(58) Field of Classification Search
CPC ............................... C07J 21/00; C07J 43/003
USPC .................... 540/15, 28, 44, 47, 108
See application file for complete search history.

(56) References Cited

U.S. PATENT DOCUMENTS

| | | | |
|---|---|---|---|
| 4,871,724 A | 10/1989 | Groen et al. | |
| 4,912,097 A | 3/1990 | Teutsch et al. | |
| 5,173,483 A | 12/1992 | Grandadam et al. | |
| 5,273,971 A | 12/1993 | Scholz et al. | |
| 5,336,686 A | 8/1994 | Nedelec et al. | |
| 5,854,235 A | 12/1998 | Hamersma et al. | |
| 6,005,124 A | 12/1999 | Brands et al. | |
| 6,020,328 A | 2/2000 | Cook et al. | |
| 6,503,895 B2 | 1/2003 | Schwede et al. | |
| 6,768,014 B2 | 7/2004 | Kim et al. | |
| 6,900,193 B1 | 5/2005 | Kim et al. | |
| 8,278,469 B2 | 10/2012 | Schwede et al. | |
| 8,673,968 B2 | 3/2014 | Nickisch et al. | |
| 2010/0273759 A1 | 10/2010 | Nickisch et al. | |
| 2012/0232042 A1 | 9/2012 | Klar et al. | |
| 2012/0258941 A1 | 10/2012 | Klar et al. | |
| 2013/0005697 A1 | 1/2013 | Schwede et al. | |
| 2013/0072464 A1 | 3/2013 | Schwede et al. | |

FOREIGN PATENT DOCUMENTS

| | | |
|---|---|---|
| EP | 0 549 041 | 6/1993 |
| WO | 99/45022 | 9/1999 |
| WO | 2008/058767 | 5/2008 |
| WO | 2011/005929 | 1/2011 |
| WO | 2013016725 | 1/2013 |

OTHER PUBLICATIONS

Nickisch et al. "Synthesis and biological evaluation of partially fluorinated antiprogestins and mesoprogestins" Steroids, vol. 78, 255-267, 2013.
Rao et al. "New 11 B-aryl-substituted Steroids Exhibit Both Progestational and Antiprogestational Activity" Steroids 63:523-530, 1998.
Morphy et al., "Designed Multiple Ligands. An Emerging Drug Discovery Paradigm." J. Med. Chem. (2005), 48, 6523-6543.
Morphy et al., "The Physicochemical Challenges of Designing Multiple Ligands." J. Med. Chem. (2006), 49, 4961-4970.
Woo et al. "First Dual Aromatase-Sulfatase Inhibitors." J. Med. Chem. (2003), 46, 3193-3196.
Wood et al. "A letrazole-based dual aromatase-sulphatase inhibitor with in vivo activity." J. Steroid Biochem Mol Biol. (2005), 94, 123-130.
Numazawa et al. "Inhibition of Estrone sulfatase by aromatic inhibitor-based estrogen 3-sulfamates." Steroids (2006), 71, 371-379.
Jackson et al. "Dual aromatic-sulfatase inhibitors based on the anastrozole template: synthesis, in vitro SAR, molecular modeling and in vivo activity." Org. Biomol. Chem. (2007), 5, 2940-2952.
Woo et al. "Dual Aromatase-Sulfatase Inhibitors." J. Med. Chem. (2007), 50, 3540-3560.
Klijn et al. "Progesterone antagonists and progesterone receptor modulators in the treatment of breast cancer." Steroids (2000), 65, 825-830.
Wiehle et al. Anti-progestins suppress the growth of established tumors induced by 7,12-dimethylbenz(a) anthracene: Comparison between RU486 and a new 21-substituted-19-norprogestin. Oncology Reports, (2007), 18, 167-174.
Brodie et al. "Aromatase Inhibitors in advanced breast cancer: Mechanism of action and clinical implications." J. Steroid Biochem. Molec. Biol. (1998), 66, 1-10.
Furet et al. "Aromatase Inhibitors: Synthesis, biological activity, and binding mode of azole-type compounds." J. Med. Chem. (1993), 36, 1393-1400.
Teutsch et al. "Synthesis of a fluorescent steroid derivative with high affinities for the glucocorticoid and progesterone receptors." Steroids (1994), 59, 22-26.
Rao et al. A practical large-scale synthesis of 17-acetoxy-11-(4-N,N-dimethylaminophenyl)-19-norpregna-4,9-diene-3,20-dione (CDB-2914). Steroids (2000), 65, 395-400.
Giangrande et al. "The Opposing Transcriptional Activities of the Two Isoforms of the Human Progesterone Receptor Are Due to Differential Cofactor Binding." Mol Cell Biol (2000) 20:3102-3115.
Jiang et al. "New progesterone receptor antagonists: Phosphorus-containing 11β-aryl-substituted steroids." Bioorg Med Chem (2006) 14:6726-6732.
International Search Report and Written Opinion from PCT/US14/41002, issued Mar. 6, 2015, Evestra Inc., pp. 1-14.

*Primary Examiner* — Brenda Coleman
(74) *Attorney, Agent, or Firm* — Meyertons, Hood, Kivlin, Kowert & Goetzel, P.C.; Eric B. Meyertons

(57) ABSTRACT

Described herein are imidazolyl compounds which either act as pure antiprogestins and methods of using such pure antagonists for gynecological indications and breast cancer.

17 Claims, 1 Drawing Sheet

IMIDAZOLYL PROGESTERONE ANTAGONISTS

BACKGROUND OF THE INVENTION

1. Field of the Invention

The present invention relates to novel compounds that exhibit progesterone antagonism without any sign of partial agonistic activity. Such compounds have application in fertility control and the treatment of hormone dependent breast cancer. The present invention also relates to processes of preparation and the use in therapy of such novel compounds.

2. Description of the Relevant Art

In the past, progesterone antagonists have been postulated to be of potential benefit in the treatment of a variety of diseases including breast cancer and different forms of fertility control.

Up to now, only two compounds belonging to this class have been approved for clinical use. The prototype antagonist, Mifepristone (see FIG. 1), is indicated for the induction of abort and Ulipristal is approved for postcoital fertility control.

Both compound are characterized as progesterone receptor modulators indicating that there might be a partial agonistic component contributing to their overall activity.

Compounds that lack any partial agonistic activity whatsoever should exhibit a greater activity in the approved indications and potentially also in the treatment of breast cancer.

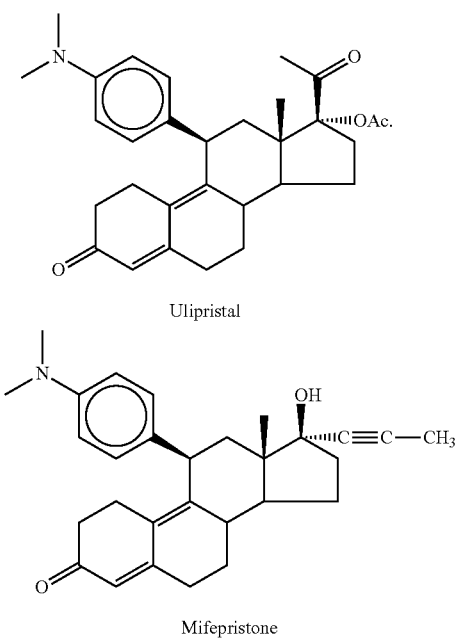

FIG. 1

Ulipristal

Mifepristone

There is the general understanding that the substituent in the 11' position is responsible for the progesterone receptor profile (Nickisch et al Steroids Vol 78, 255-267, 2013). Whereas the dimethyl amino group as found in Mifepristone and Ulipristal leads to compounds with a predominant antagonistic activity, aromatic substituents like furans or pyridins lead to compounds with a strong partial agonistic component (EP000002417148) that have potential in the treatment of gynecological indications like endometriosis but not for postcoital fertility control and breast cancer.

Substituents in the 17 position have an influence on the binding selectivity for the progesterone and glucocorticoid receptor. 17 moieties have been reported to lead to a high selectivity for the progesterone receptor are e.g. the perfloualkyl alkyl group as originally described in DE 197 06061.

Different 11 substituents carrying the perfluoralkyl group in the 17 position have been reported later e.g. WO 2008058767, WO 2011005929, WO 2011009530, WO 2011009531, WO 2011009534, WO 2011098436 and WO 2011098437.

Other 17 substituents with good specificity to the progesterone receptor include 17-spirofuran-3'-ylidene as described in EP 549041, 17 spirolactones as described in EP 558416 and difluro 17-spirofuran-3'yliden as described in WO 20100118025.

In those patents a large variety of 11' substituents including different heteroycles have been described, but surprisingly 11'N imidazols have not been reported, lost likely caused by the fact that such molecules need special methods for their synthesis, although the general structure has been claimed by Cook et al. In WO99/45022.

It was therefore even more surprising that the described 11'N Imidazols exhibit very potent antiprogestational activity lacking any agonistic component, what make them ideal candidates for the induction of labor, postcoital fertility control, termination of pregnancy and breast cancer

SUMMARY OF THE INVENTION

In one embodiment, a progesterone antagonist has the structure of formula (I):

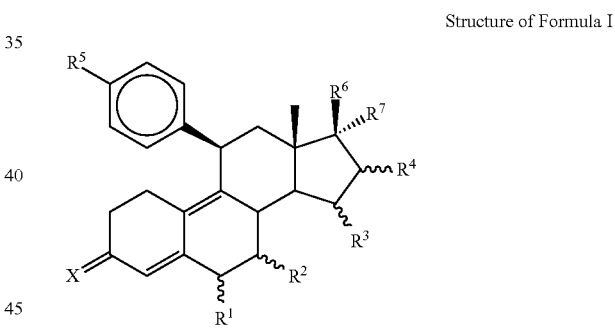

Structure of Formula I

In which:
X is O or $H_2$
$R^1$ is a hydrogen atom, a straight-chain $C_1$-$C_5$ alkyl group, a branched $C_1$-$C_5$ alkyl group, a $C_3$-$C_5$ cycloalkyl group or a halogen atom;
$R^2$ is a hydrogen atom, a straight-chain $C_1$-$C_5$ alkyl group, a branched $C_1$-$C_5$ alkyl group, a $C_3$-$C_5$ cycloalkyl group or a halogen atom; or
$R^1$ and $R^2$ together are a methylene group,
$R^3$ is a hydrogen atom, a straight-chain $C_1$-$C_5$ alkyl group, a branched $C_1$-$C_5$ alkyl group, a $C_3$-$C_5$ cycloalkyl group or a halogen atom;
$R^4$ is a hydrogen atom, a straight-chain $C_1$-$C_5$ alkyl group, a branched $C_1$-$C_5$ alkyl group, a $C_3$-$C_5$ cycloalkyl group or a halogen atom; or
$R^3$ and $R^4$ together are an additional bond or a methylene group,
$R^5$ an N imidazolyl group that could be optionally substituted by one or more alkyl groups
$R^6$ stands for a free, etherified or esterified hydroxyl group, $R^7$ stands for a radical of formula $C_nF_mH_o$ whereby n is 2, 3, 4, 5 or 6 with m≥1 and m+o=2n+1 or 2n−1 or 2n−3

In an embodiment, a progesterone antagonist has the structure of formula (I):
where
X is O;
$R^1$ and $R^2$ are hydrogen atoms;
$R^3$ and $R^4$ are hydrogen atoms
$R^5$ is an N imidazolyl group;
$R^6$ is a hydroxyl group,
$R^7$ stands for a radical of formula $C_nF_mH_o$ whereby n is 2, 3, 4, 5 or 6 with m≥1 and m+o=2n+1 or 2n−1 or 2n−3.

In an embodiment, a progesterone antagonist has the structure of formula (I):
where
X is O;
$R^1$ and $R^2$ together are a methylene group,
$R^3$ and $R^4$ together are an additional bond or a methylene group,
$R^5$ is an N imidazolyl group;
$R^6$ is a hydroxyl group,
$R^7$ stands for a radical of formula $C_nF_mH_o$ whereby n is 2, 3, 4, 5 or 6 with m≥1 and m+o=2n+1 or 2n−1 or 2n−3.

In an embodiment, a progesterone antagonist has the structure of formula (I):
where
X is O;
$R^1$ and $R^2$ are hydrogen atoms;
$R^3$ and $R^4$ are hydrogen atoms
$R^5$ is an N imidazolyl group;
$R^6$ is a hydroxyl group,
$R^7$ stands for a radical of formula $C_nF_mH_o$ whereby n is 2, 3, 4, 5 or 6 with m≥1 and m+o=2n+1.

In an embodiment, a progesterone antagonist has the structure of formula (I):
where
X is O;
$R^1$ and $R^2$ are hydrogen atoms;
$R^3$ and $R^4$ are hydrogen atoms
$R^5$ is an N imidazolyl group;
$R^6$ is a hydroxyl group,
$R^7$ stands for a radical of formula $C_nF_mH_o$ whereby n is 2, 3, 4, 5 or 6 with m≥1 and m+o=2n−1.

In an embodiment, a progesterone antagonist has the structure of formula (I):
where
X is O;
$R^1$ and $R^2$ are hydrogen atoms;
$R^3$ and $R^4$ are hydrogen atoms
$R^5$ is an N imidazolyl group;
$R^6$ is a hydroxyl group,
$R^7$ stands for a radical of formula $C_nF_mH_o$ whereby n is 2, 3, 4, 5 or 6 with m≥1 and m+o=2n−3.

In an embodiment, a progesterone antagonist has the structure:

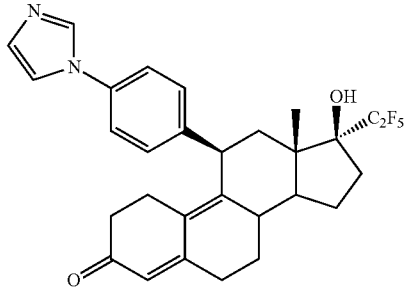

Ia

In an embodiment, a progesterone antagonist has the structure:

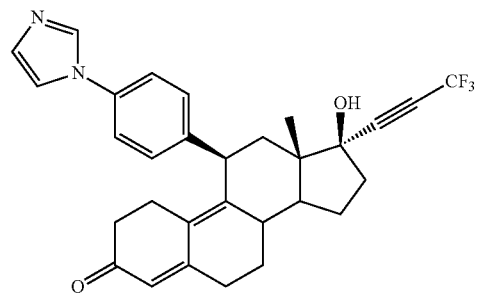

Ib

In an embodiment, a progesterone antagonist has the structure:

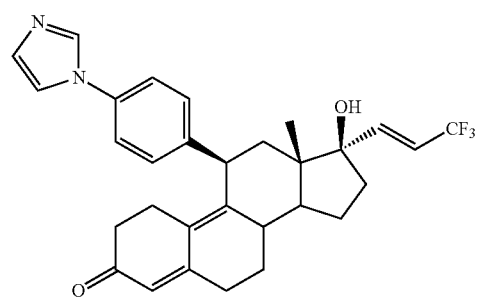

Ic

In an embodiment, a progesterone antagonist has the structure:

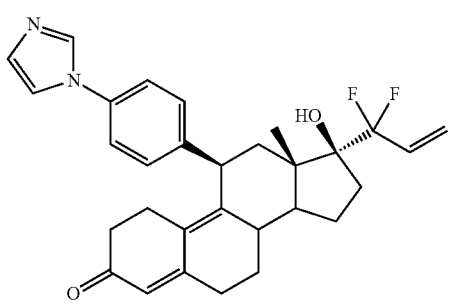

Id

In an embodiment, a progesterone antagonist has the structure of formula (I):

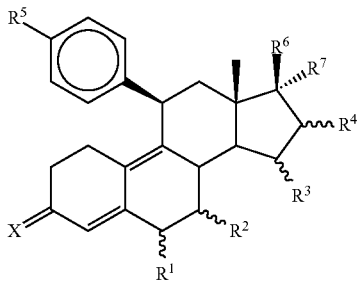

Wherein:

X is O or $H_2$ $R^1$ is a hydrogen atom, a straight-chain $C_1$-$C_5$ alkyl group, a branched $C_1$-$C_5$ alkyl group, a $C_3$-$C_5$ cycloalkyl group or a halogen atom;

$R^2$ is a hydrogen atom, a straight-chain $C_1$-$C_5$ alkyl group, a branched $C_1$-$C_5$ alkyl group, a $C_3$-$C_5$ cycloalkyl group or a halogen atom; or $R^1$ and $R^2$ together are a methylene group, $R^3$ is a hydrogen atom, a straight-chain $C_1$-$C_5$ alkyl group, a branched $C_1$-$C_5$ alkyl group, a $C_3$-$C_5$ cycloalkyl group or a halogen atom;

$R^4$ is a hydrogen atom, a straight-chain $C_1$-$C_5$ alkyl group, a branched $C_1$-$C_5$ alkyl group, a $C_3$-$C_5$ cycloalkyl group or a halogen atom; or $R^3$ and $R^4$ together are an additional bond or a methylene group;

$R^5$ an N imidazolyl group that is optionally substituted by one or more alkyl groups; and $R^6$ and $R^7$ are

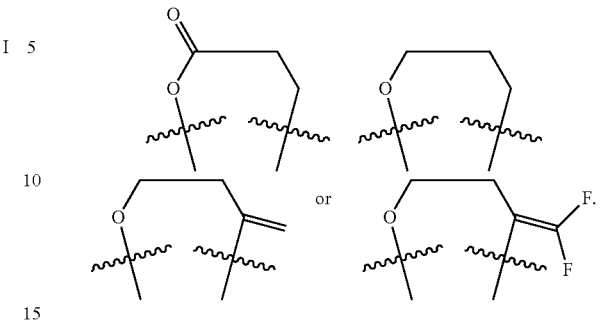

The wavy lines represent that the substituent in question can be in α- or β-position.

In an embodiment, a progesterone antagonist has the structure of formula (I):
where
X is O
$R^1$ and $R^2$ are hydrogen atoms;
$R^3$ and $R^4$ are hydrogen atoms;
$R^5$ an N imidazolyl group that is optionally substituted by one or more alkyl groups; and
$R^6$ and $R^7$ are

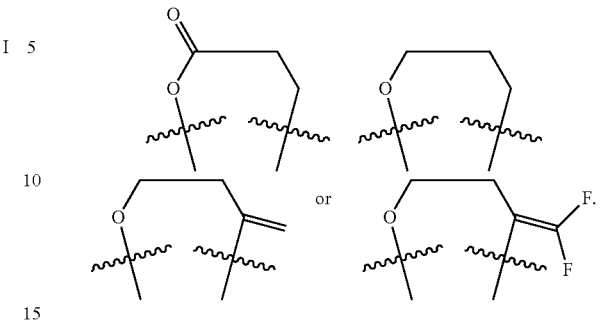

In an embodiment, a progesterone antagonist has the structure of formula (I):
where
X is O
$R^1$ and $R^2$ together are a methylene group,
$R^3$ and $R^4$ together are an additional bond or a methylene group;
$R^5$ an N imidazolyl group that is optionally substituted by one or more alkyl groups; and
$R^6$ and $R^7$ are

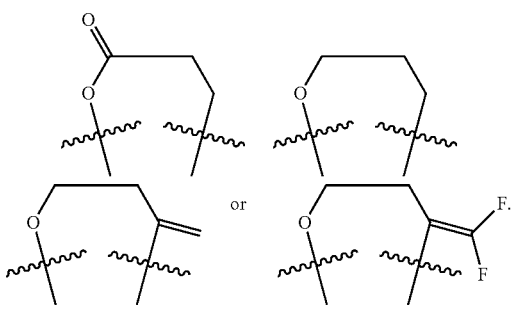

In an embodiment, a progesterone antagonist has the structure of formula (I):
where
X is O
$R^1$ and $R^2$ are hydrogen atoms;
$R^3$ and $R^4$ are hydrogen atoms;
$R^5$ an N imidazolyl group that is optionally substituted by one or more alkyl groups; and
$R^6$ and $R^7$ are

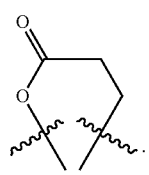

In an embodiment, a progesterone antagonist has the structure of formula (I):
where
X is O
$R^1$ and $R^2$ are hydrogen atoms;
$R^3$ and $R^4$ are hydrogen atoms;
$R^5$ an N imidazolyl group that is optionally substituted by one or more alkyl groups; and $R^6$ and $R^7$ are In an embodiment, a progesterone antagonist has the structure of formula (I):
where
X is O
$R^1$ and $R^2$ are hydrogen atoms;
$R^3$ and $R^4$ are hydrogen atoms;
$R^5$ an N imidazolyl group that is optionally substituted by one or more alkyl groups; and
$R^6$ and $R^7$ are In an embodiment, a progesterone antagonist has the structure:

Ie

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
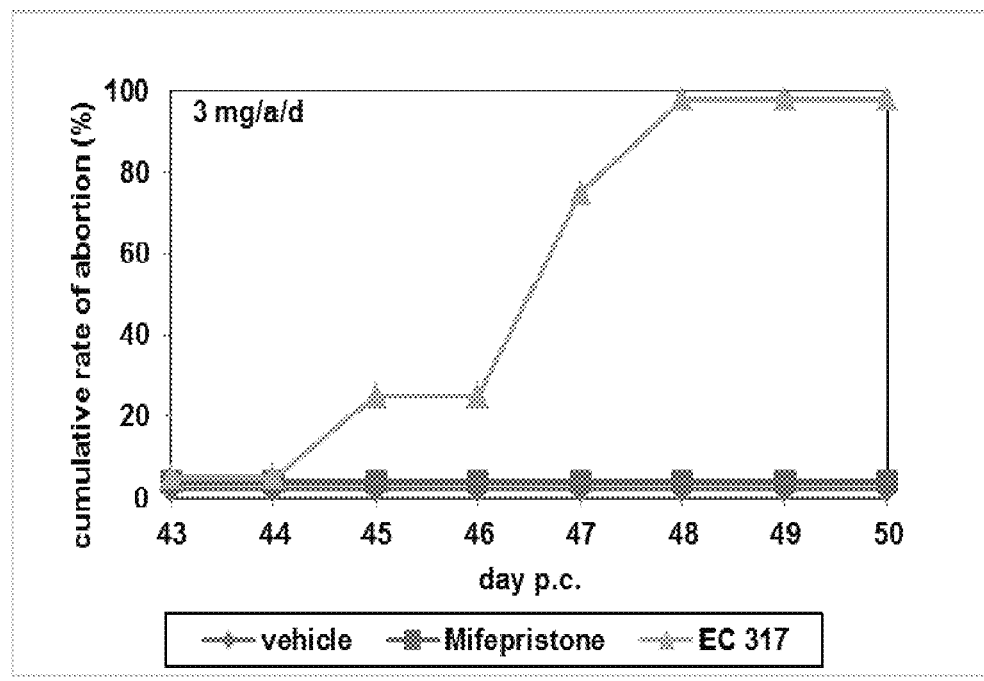
FIG. 1 is a graph of the cumulative rate of abortion when 3 mg/a/d of a compound of structure 1 is tested using the pregnant guinea pig model.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

Unless defined otherwise, all technical and scientific terms used herein have the same meaning as commonly understood by one of ordinary skill in the art.

The term "alkyl" as used herein generally refers to a chemical substituent containing the monovalent group $C_nH_{2n}$, where n is an integer greater than zero. In some embodiments n is 1 to 12. The term "alkyl" includes a branched or unbranched monovalent hydrocarbon radical. Examples of alkyl radicals include, but are not limited to: methyl, ethyl, propyl, isopropyl, butyl, iso-butyl, sec-butyl, pentyl, 3-pentyl, hexyl, heptyl, octyl, nonyl, decyl, undecyl, dodecyl. When the alkyl group has from 1-6 carbon atoms, it is referred to as a "lower alkyl." Suitable lower alkyl radicals include, but are not limited to, methyl, ethyl, n-propyl, i-propyl, 2-propenyl (or allyl), n-butyl, t-butyl, and i-butyl (or 2-methylpropyl).

The term "substituted alkyls" as used herein generally refers to alkyl radicals that include one or more functional groups attached to any carbon of the alkyl radical. Functional groups include, but are not limited to, aryl, aralkyl, acyl, halogens, hydroxyl, amino, alkylamino, acylamino, acyloxy, alkoxy, and mercapto. As used herein the term "substituted lower alky" refers to an alkyl residue having from 1-6 carbon atoms and one or more functional groups attached to any carbon of the alkyl radical.

The term "alkoxy" generally refers to an —OR group, where R is a lower alkyl, substituted lower alkyl, aryl, substituted aryl, aralkyl or substituted aralkyl. Suitable alkoxy radicals include, but are not limited to, methoxy, ethoxy, phenoxy, t-butoxy, methoxyethoxy, and methoxymethoxy.

The term "acyloxy" is used herein to refer to an organic radical derived from an organic acid by the removal of a hydrogen. The organic radical can be further substituted with one or more functional groups including, but not limited to, alkyl, aryl, aralkyl, acyl, halogen, amino, thiol, hydroxyl, alkoxy. etc. Suitable acyloxy groups include, for example, acetoxy, i.e., $CH_3COO-$, which is derived from acetic acid.

The term "halogen" is used herein to refer to fluorine, bromine, chlorine and iodine atoms.

The term "hydroxyl" is used herein to refer to the group —OH.

The term "alkylacyl" denotes groups —C(O)R where R is alkyl or substituted alkyl, aryl or substituted aryl as defined herein.

The term "cycloalkylacyl" denotes groups —C(O)R where R is a cycloalkyl or substituted cycloalkyl such as, for example, cyclopropylacyl-, cyclopentylacyl and cyclohexylacyl.

The term "aryl" is used to refer to an aromatic substituent which may be a single ring or multiple rings which are fused together, linked covalently, or linked to a common group such as an ethylene moiety. Aromatic ring(s) include but are not limited to phenyl, naphthyl, biphenyl, diphenylmethyl, and 2,2-diphenyl-1-ethyl. The aryl group may also be substituted with substituents including, but not limited to, alkyl groups, halogen atoms, nitro groups, carboxyl groups, alkoxy, and phenoxy to give a "substituted aryl group." Substituents may be attached at any position on the aryl radical which would otherwise be occupied by a hydrogen atom.

The term "fluorinated alkynyl" as used herein generally refers to alkynyl radicals that include one or more fluorine atoms attached to any carbon of the alkynyl radical in place of a hydrogen atom.

The term "pharmaceutically acceptable salts" includes salts prepared from by reacting pharmaceutically acceptable non-toxic bases or acids, including inorganic or organic bases, with inorganic or organic acids. Pharmaceutically acceptable salts may include salts derived from inorganic bases include aluminum, ammonium, calcium, copper, ferric, ferrous, lithium, magnesium, manganic salts, manganous, potassium, sodium, zinc, etc. Examples include the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, etc.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention Experimental Section:

Specific examples of compounds having the formula (I) include the following compounds:

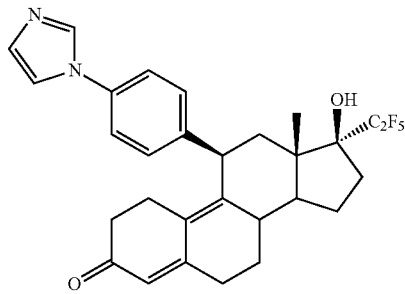

Ia

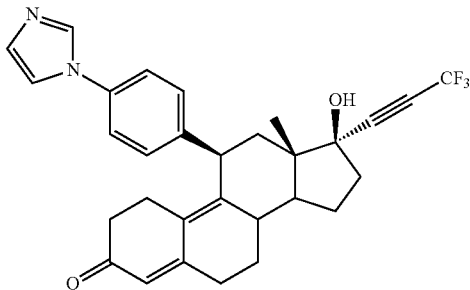

Ib

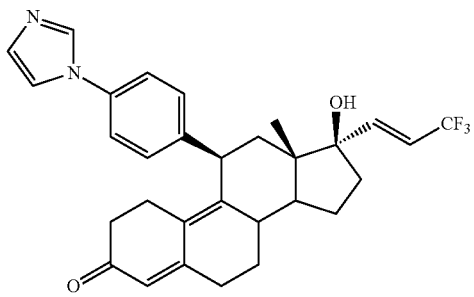

Ic

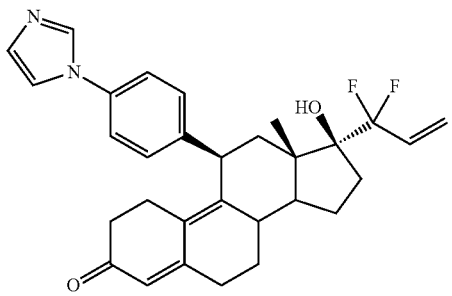

Id

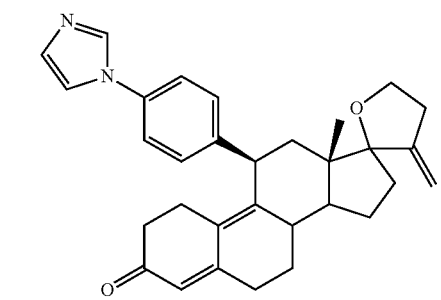

Ie

Synthesis of compounds Ia, Ib, Ic, Id, Ie may be accomplished according to the following schemes.

Compound I may be synthesized by following the scheme outlined below.

Scheme 1

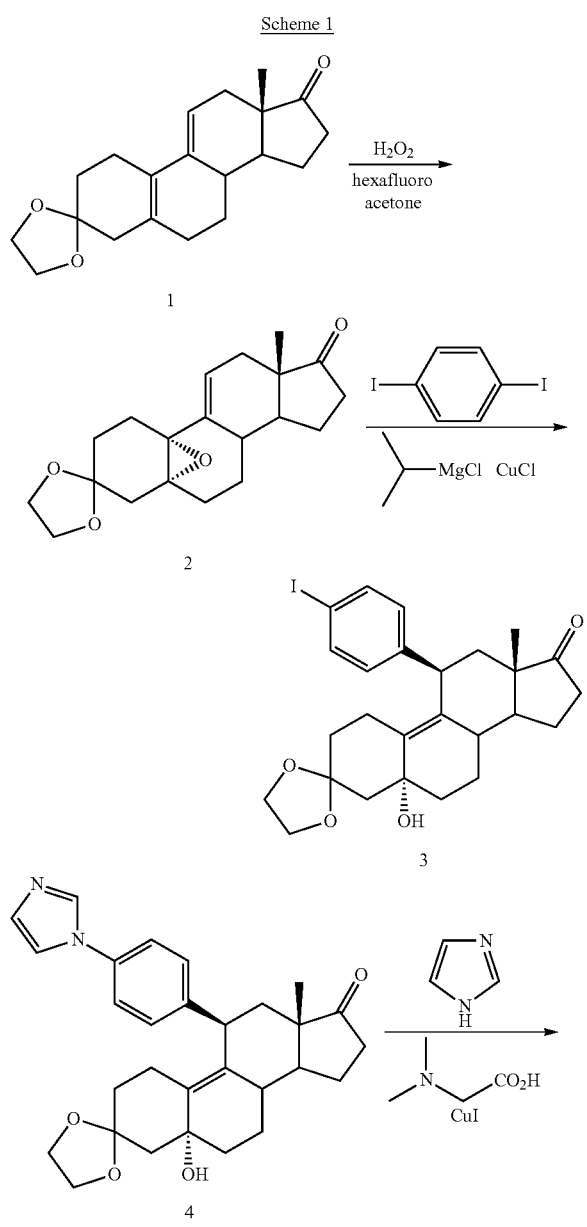

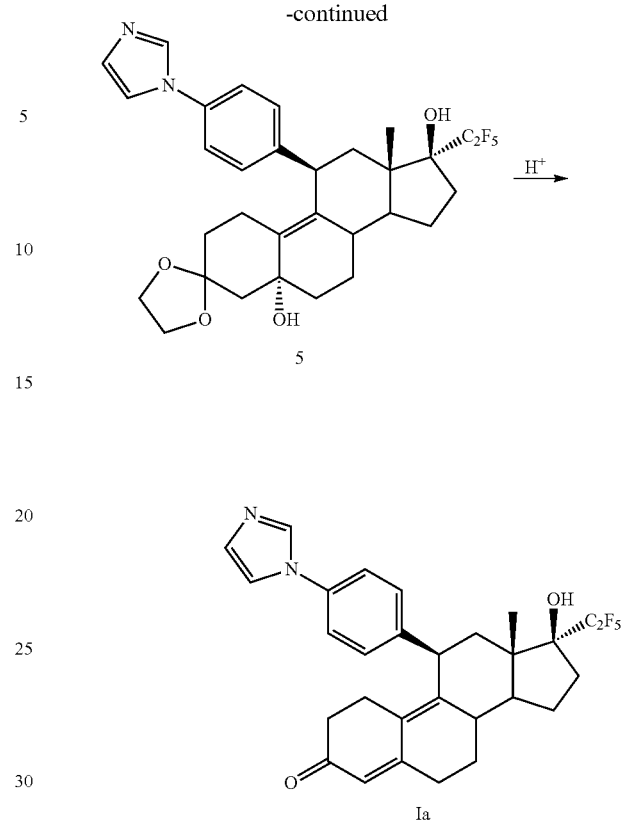

Intermediate 2 may be synthesized following the procedure reported in Steroids, 1998, 63, 523. Intermediate 3 is prepared by an arylcuprate addition on 2 generated by the reaction of 1,4-diiodo benzene, isopropyl magnesium chloride and catalytic amounts of cuprous chloride. The aryl iodo derivative 3 thus obtained was coupled with imidazole following Ullman reaction conditions employing cuprous iodide as the copper catalyst and N, N-dimethyl glycine as the ligand.

Pentafluorolithium addition on the 17-keto group of compound 4 followed by hydrolysis afforded compound Ia.

Compounds Ia and Ib may be synthesized according to the following scheme.

Scheme 2

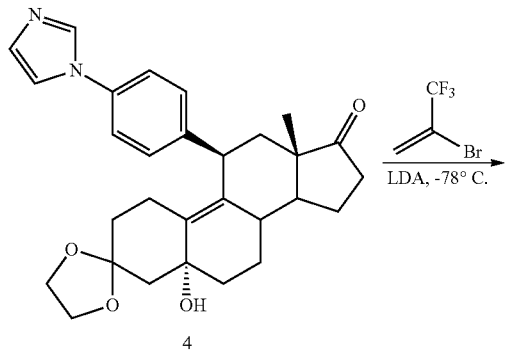

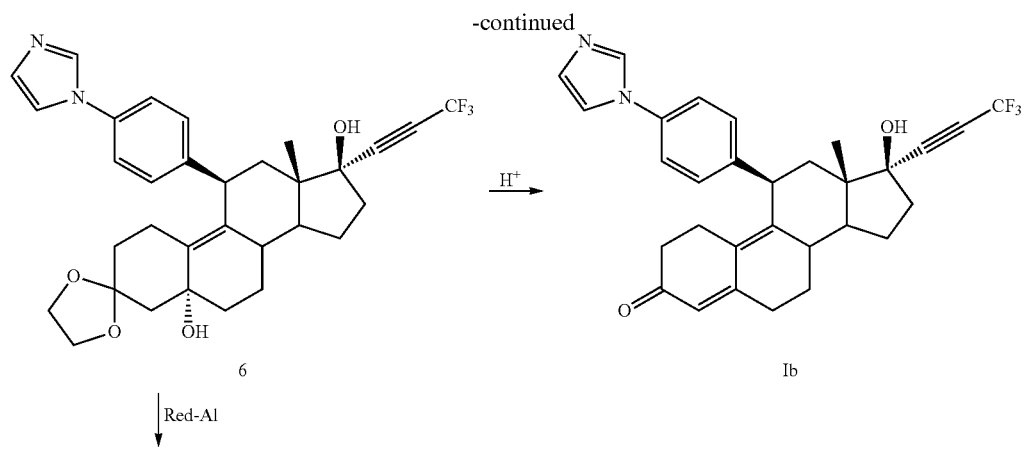

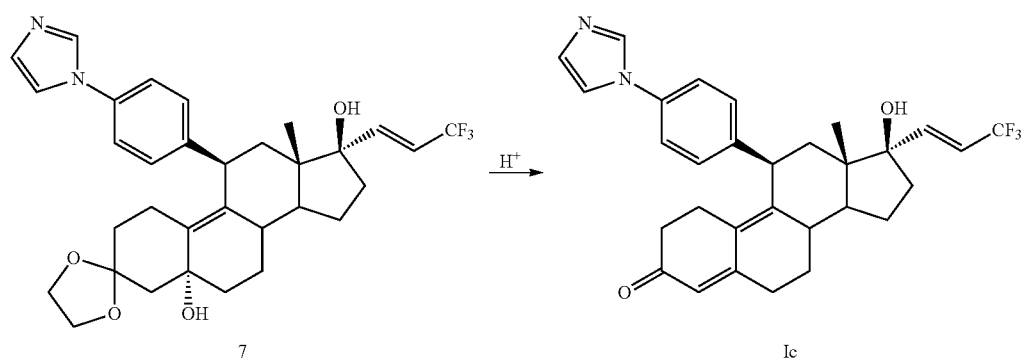

3,3,3-trifluoropropynyl lithium, generated by treating 2-bromo-3,3,3-trifluoropropene with LDA at −78° C. was added to the 17-ketone of intermediate 3 to form compound 6 which on acid hydrolysis afforded compound Ib. Red-Al reduction of intermediate 6 gave compound 7, which on hydrolysis using 4N hydrochloric acid furnished compound Ic.

Compound Id may be prepared following the scheme outlined below.

Scheme 3

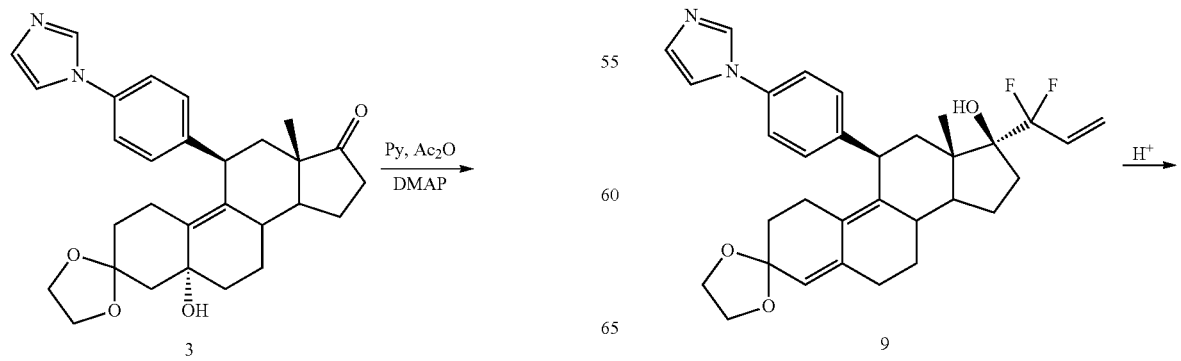

15
-continued

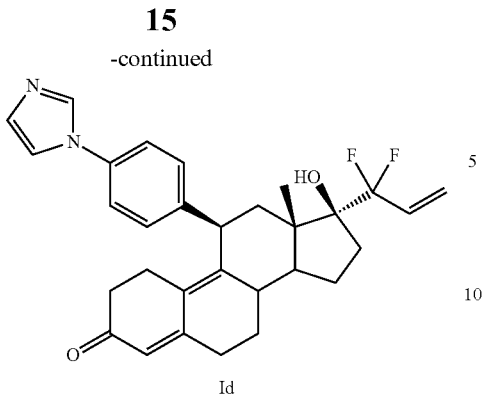

Id

Intermediate 3 was dehydrated at 5 position using excess acetic anhydride and pyridine. The resulting crude material was used as such for the difluoroallyllithium addition at −100° C. to generate compound 9, which upon acid hydrolysis afforded compound IV.

Synthesis of compound Ie may be accomplished following the procedure outlined in Scheme 4.

Scheme 4

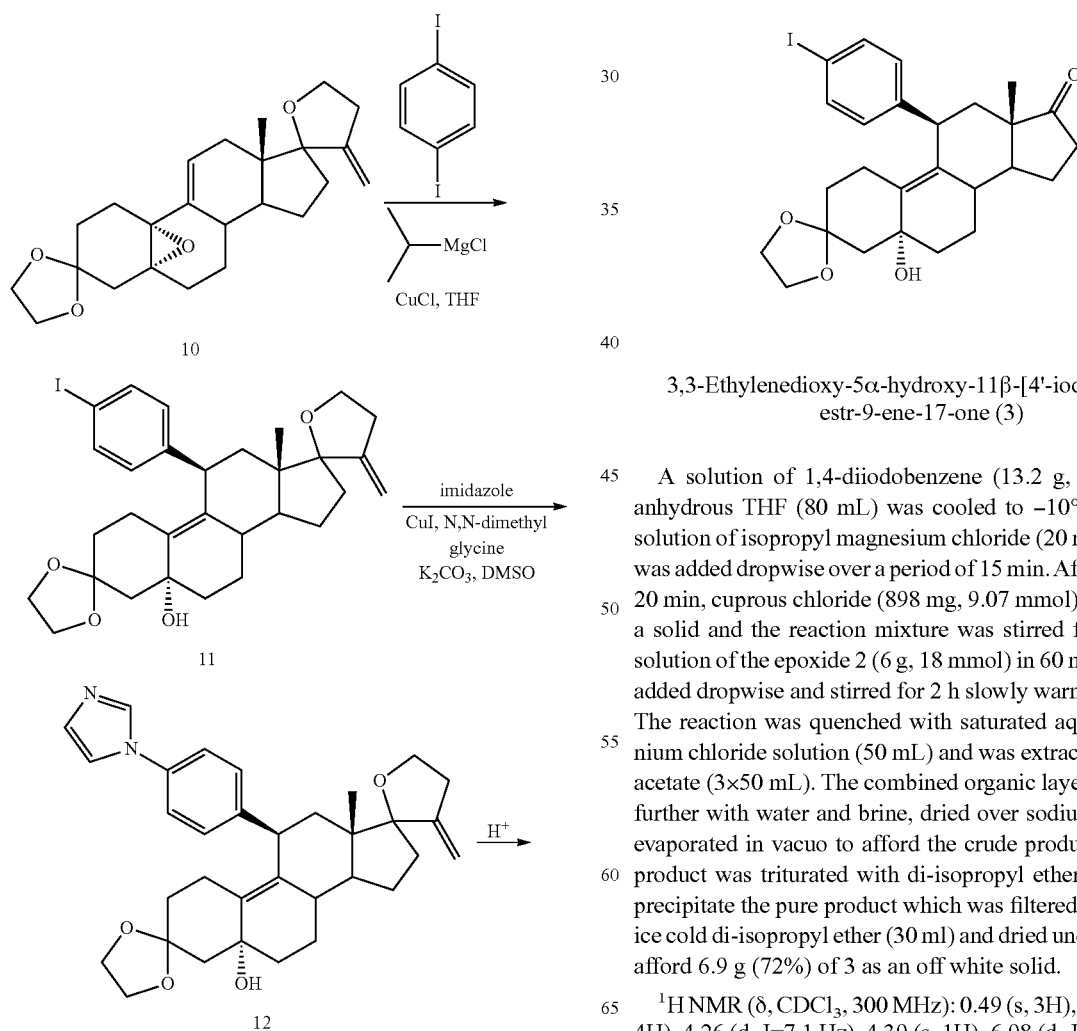

16
-continued

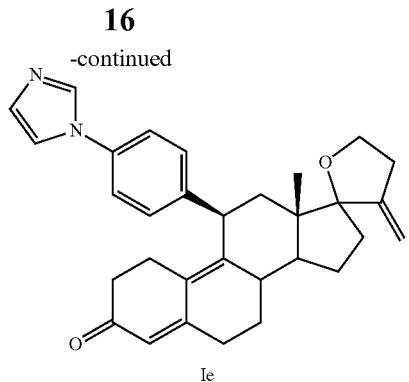

Ie

Intermediate 10 was prepared following the procedure reported by Jiang, et. al in Bioorg Med Chem (2006) 14: 6726-6732. An aryl cuprate addition on epoxide 10 using 1,4-diiodo benzne, isopropyl magnesium chloride and cuprous chloride afforded compound 11.

An Ullman coupling of intermediate 11 with imidazole using cuprous iodide as the catalyst, N, N-dimethyl glycine as the ligand and potassium carbonate as the base furnished intermediate 12 which on acid hydrolysis afforded compound Ie.

3,3-Ethylenedioxy-5α-hydroxy-11β-[4'-iodophenyl]-estr-9-ene-17-one (3)

A solution of 1,4-diiodobenzene (13.2 g, 40 mmol) in anhydrous THF (80 mL) was cooled to −10° C. as a 2 M solution of isopropyl magnesium chloride (20 mL, 40 mmol) was added dropwise over a period of 15 min. After stirring for 20 min, cuprous chloride (898 mg, 9.07 mmol) was added as a solid and the reaction mixture was stirred for 30 min. A solution of the epoxide 2 (6 g, 18 mmol) in 60 ml of THF was added dropwise and stirred for 2 h slowly warming to 10° C. The reaction was quenched with saturated aqueous ammonium chloride solution (50 mL) and was extracted with ethyl acetate (3×50 mL). The combined organic layer was washed further with water and brine, dried over sodium sulfate and evaporated in vacuo to afford the crude product. The crude product was triturated with di-isopropyl ether (120 mL) to precipitate the pure product which was filtered, washed with ice cold di-isopropyl ether (30 ml) and dried under vacuum to afford 6.9 g (72%) of 3 as an off white solid.

$^1$H NMR (δ, CDCl$_3$, 300 MHz): 0.49 (s, 3H), 3.88-4.04 (m, 4H), 4.26 (d, J=7.1 Hz), 4.39 (s, 1H), 6.98 (d, J=8.1 Hz, 2H), 7.57 (d, J=8.4 Hz, 2H).

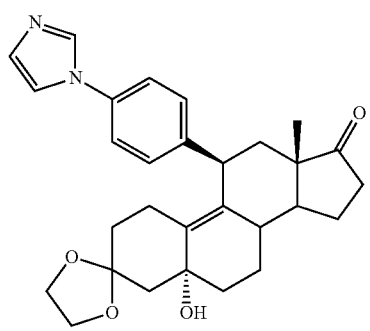 [SMILES: C[C@]12C[C@H](c3ccc(-n4ccnc4)cc3)C3=C4CCC5(C[C@]4(O)CCC3C1CCC2=O)OCCO5]

3,3-Ethylenedioxy-5α-hydroxy-11β-[4'-(1-imidazolyl)phenyl]-estr-9-ene-17-one (4)

A mixture of compound 3 (9.7 g, 18 mmol), imidazole (1.4 g, 20 mmol), cuprous iodide (346 mg, 1.8 mmol), N, N-dimethyl glycine (374 mg, 3.6 mmol) and potassium carbonate (5 g, 36 mmol) in anhydrous DMSO (10 mL) was degassed three times applying vacuum and nitrogen and was immersed in to a preheated oil bath at 110° C. The reaction mixture was heated for 60 h. After cooling to room temperature, the reaction mixture was diluted with ethyl acetate (150 mL) and filtered through a Celite pad. The filtrate was transferred to a reparatory funnel and was washed with water, brine and dried over anhydrous sodium sulfate. The solvent was removed under vacuum to afford the crude product, which on purification by chromatography on SiO$_2$ column eluting with 30% acetone in dichloromethane gave 7.6 g (91%) of required product 4 as a pale yellow solid.

$^1$H NMR (δ, CDCl$_3$, 300 MHz): 0.51 (s, 3H), 3.92-4.04 (m, 4H), 4.37-4.39 (m, 2H), 7.19 (s, 1H), 7.27-7.35 (m, 5H), 7.84 (s, 1H).

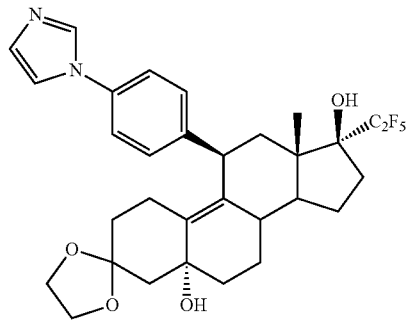

3,3-Ethylenedioxy-5α,17β-dihydroxy-17-(1,1,2,2,2-pentafluoroethyl)-11β-(4'-(1-imidazolyl)phenyl)-estr-9-ene (5)

Pentafluoroiodoethane (3.9 g, 16 mmol) was condensed in to a solution of compound 4 (1.3 g, 2.7 mmol) in toluene (45 mL) kept at −78° C. A 1.5 M solution of methyl lithium-lithium bromide complex (8.9 mL, 13.5 mmol) was added dropwise over a period of 15 min. The resulting reaction mixture was stirred at −78° C. for an hour and allowed to stir at 0° C. for another 1 h. The reaction was quenched by the addition of saturated sodium bicarbonate solution (30 mL). Extracted with ethyl acetate (2×50 mL) and the combined organic layer were washed once with water, brine and dried over sodium sulfate. The solvent was removed under vacuum to obtain the crude product, which on purification by chromatography on SiO$_2$ column eluting with 10% acetone in dichloromethane gave 1.28 g (80%) of required product 5 as a pale yellow solid.

$^1$H NMR (δ, CDCl$_3$, 300 MHz): 0.60 (s, 3H), 3.89-4.04 (m, 4H), 4.37 (s, 2H), 7.18 (s, 1H), 7.27-7.32 (m, 5H), 7.67 (s, 1H).

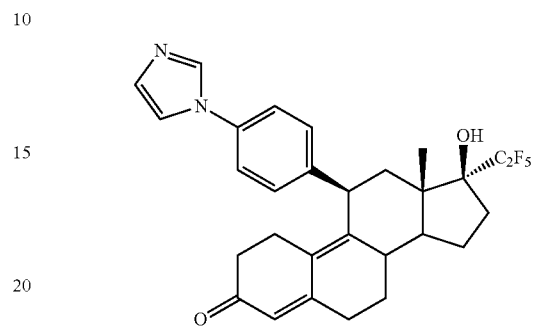

11β-(4'-(1-imidazolyl)phenyl)-17β-hydroxy-17-(1,1,2,2,2-pentafluoroethyl)-estra-4,9-diene-3-one (Ia)

A solution of compound 5 (1 g, 1.68 mmol) in methanol (10 mL) was cooled to 0° C. as 5N hydrochloric acid (1.6 mL, 8.4 mmol) was added dropwise. The reaction mixture was stirred for an hour warming to room temperature. Quenched by the careful addition of saturated sodium bicarbonate solution and extracted with ethyl acetate (2×25 mL). Combined organic layers were washed with water, brine and dried over anhydrous sodium sulfate. The solvent was removed in vacuo to obtain the crude product, which on purification by chromatography on SiO$_2$ column eluting with 10% acetone in dichloromethane gave 0.8 g (90%) of required compound Ia as an off white solid.

$^1$H NMR (δ, CDCl$_3$, 300 MHz): 0.68 (s, 3H), 4.48 (d, J=6.6 Hz, 1H), 5.79 (s, 1H), 7.18 (s, 1H), 7.23-7.30 (m, 5H), 7.62 (s, 1H).

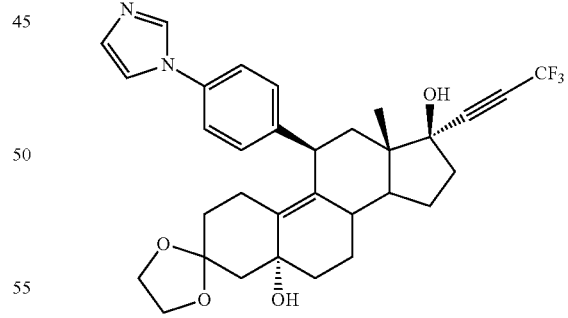

3,3-Ethylenedioxy-5α,17β-dihydroxy-17-(3,3,3-trifluoro-1-propynyl)-11β-{4'-[1' imidazolyl)phenyl}-estr-9-ene (6)

Freshly prepared lithium diisopropylamide solution made by the addition of n-BuLi (6.4 mL, 2.5 M, 16 mmol) to diisopropylamine (1.6 g, 16 mmol) in THF (20 mL) at −78° C. was added to a solution of 2-bromo-3,3,3-trifluoropropene (2.4 g, 14 mmol) in THF (15 mL) at −78° C. The resulting purple solution was stirred at this temperature for 20 min. A solution of compound 4 (1.09 g, 2.3 mmol) in THF (10 mL) was introduced in to the reaction mixture over a period of 20 min and was stirred for 1 h at −78° C. and allowed to warm to r.t. over a period of 16 h. Reaction mixture was quenched with aqueous ammonium chloride (50 mL) and extracted with ethyl acetate (3×100 mL). The combined organic layer was washed further with water and brine, dried over anhydrous sodium sulfate and evaporated in vacuo to afford the crude product. Purification was performed on a silica gel column using 10% acetone in methylene chloride to afford compound 6 (1.55 g, 88%) as a brown amorphous solid.

$^1$H NMR (δ, CDCl$_3$, 300 MHz): 0.52 (s, 3H), 3.75-4.10 (m, 4H), 4.35-4.50 (m, 2H), 7.16 (s, 1H), 7.27-7.36 (m, 5H), 7.84 (s, 1H).

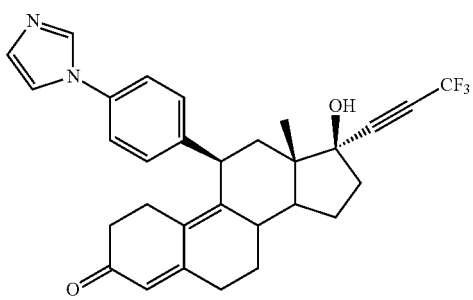 [SMILES: C[C@]12C[C@H](c3ccc(-n4ccnc4)cc3)C3=C4CCC(=O)C=C4CCC3C1CC[C@@]2(O)C#CC(F)(F)F]

11β-(4'-(1-imidazolyl)phenyl)-17β-hydroxy-17-(3,3,3-trifluoro-1-propynyl)-estra-4,9-diene-3-one (Ib)

To a solution of compound 6 (800 mg, 1.4 mmol) in methanol (10 mL) at 0° C. was added 50% sulfuric acid (0.5 mL). After stirring for 90 min, the reaction mixture was carefully quenched by the addition of saturated sodium bicarbonate solution. Extracted with ethyl acetate (2×50 mL) and the combined organic layers were washed with water, brine and dried over an sodium sulfate. The solvent was removed under vacuum to obtain the crude product which was purified on a silica column eluting with 20% acetone in methylene chloride to give compound Ib (600 mg, 84%) as a light brown amorphous solid.

$^1$H NMR (δ, CDCl$_3$, 300 MHz): 0.58 (s, 3H), 4.51 (d, J=6.5 Hz, 1H), 5.82 (s, 1H), 7.20 (s, 1H), 7.27-7.34 (m, 5H), 7.83 (s, 1H).

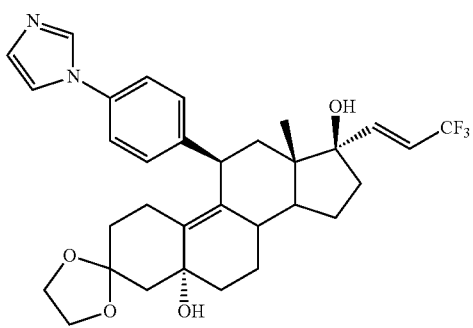 [SMILES: C[C@]12C[C@H](c3ccc(-n4ccnc4)cc3)C3=C4CCC5(C[C@]4(O)CCC3C1CC[C@@]2(O)/C=C/C(F)(F)F)OCCO5]

3,3-Ethylenedioxy-5α,17β-dihydroxy-17-(3,3,3-trifluoroprop-1(E)-enyl)-11β-{4'-[1'imidazolyl)phenyl}-estr-9-ene (7)

A solution of compound 6 (1.8 g, 3.1 mmol) in anhydrous toluene (30 mL) was cooled to −78° C. as a 65% solution of Red-Al (2.14 ml, 11 mmol) was added dropwise and the reaction mixture was stirred for 4 h at −78° C. Reaction was quenched by the addition of saturated ammonium chloride. The separated organic layer was washed with water, brine and dried over anhydrous sodium sulfate. The solvent was removed in vacuo to afford the crude product, which on purification by chromatography on silica column eluting with 20% acetone in methylene chloride gave compound 7 (1.5 g, 85%) as a brown foam.

$^1$H NMR (δ, CDCl$_3$, 300 MHz): 0.57 (s, 3H), 3.92-4.03 (m, 4H), 4.30 (d, J=6.2 Hz, 1H), 4.42 (s, 1H), 5.90-5.98 (m, 1H), 6.52 (dd, J$_1$=15.4 Hz, J$_2$=1.8 Hz 1H) 7.16-7.34 (m, 6H), 7.83 (s, 1H).

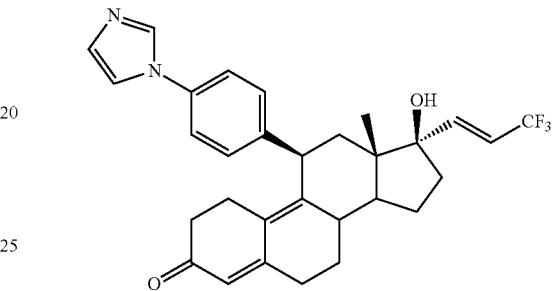

11β-(4'-(1-imidazolyl)phenyl)-17β-hydroxy-17-(3,3,3-trifluoroprop-1(E)-enyl)-estra-4,9-diene-3-one (Ic)

A solution of compound 7 (1 g, 1.5 mmol) in methanol (15 mL) was cooled to 0° C. as 5N hydrochloric acid (1.2 mL, 6.22 mmol) was added dropwise. The reaction mixture was stirred for an hour warming to room temperature. Quenched by the careful addition of saturated sodium bicarbonate solution and extracted with ethyl acetate (2×25 mL). Combined organic layers were washed with water, brine and dried over anhydrous sodium sulfate. The solvent was removed in vacuo to obtain the crude product, which on purification by chromatography on SiO$_2$ column eluting with 10% acetone in dichloromethane gave 1.06 g (67%) of required compound Ic as a pale brown solid.

$^1$H NMR (δ, CDCl$_3$, 300 MHz): 0.64 (s, 3H), 4.42 (d, J=6.8 Hz, 1H), 5.80 (s, 1H), 5.98-6.05 (m, 1H), 6.59 (dd, J$_1$=15.5 Hz, J$_2$=1.8 Hz 1H) 7.17-7.30 (m, 6H), 7.77 (s, 1H).

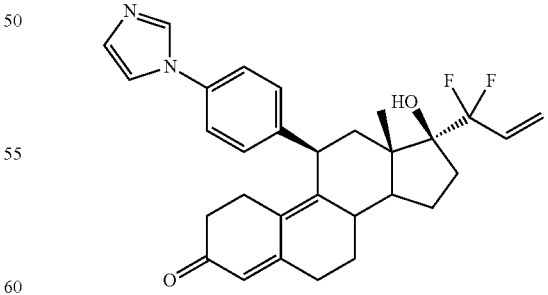

11β-(4'-(1-imidazolyl)phenyl)-17β-hydroxy-17-(1,1-difluoroprop-2-enyl)-estra-4,9-diene-3-one (Id)

To a solution of compound 4 (1.9 g, 4 mmol) in pyridine (15 mL) was added DMAP (98 mg, 0.8 mmol) followed by acetic anhydride (2.86 g, 28 mmol) and the resulting mixture was heated at 60° C. for 30 h. The solvents were removed under vacuum and the crude was quickly passed through a short pad of silica and concentrated to obtain compound 8 (1.82 g, 3.9 mmol), which was dissolved in THF-ether-pentane (4:1:1, 80 mL) mixture and was cooled to −100° C. n-BuLi (8 mL, 2.5 M, 20 mmol) was added dropwise and the reaction mixture was allowed to stir for 90 min at −95° C. and allowed to warm to room temperature over 3 h. Quenched with ammonium chloride solution (50 mL) and extracted with ethyl acetate (3×50 mL). The combined organic layer was concentrated under vacuum and the crude obtained was dissolved in methanol (20 mL) and treated with 5N hydrochloric acid (1.7 mL) at 0° C. Reaction was allowed to stir at room temperature for 2 h and was carefully quenched with saturated sodium bicarbonate solution (25 mL). Organic materials were extracted with ethyl acetate (3×30 mL) and the combined organic layers were dried over sodium sulfate, concentrated under vacuum. Purification was effected on a silica gel column using 10% acetone in methylene chloride to afford Id (400 mg, 20%) as a pale yellow amorphous solid.

$^1$H NMR (δ, CDCl$_3$, 300 MHz): 0.62 (s, 3H), 4.44-4.46 (m, 1H), 5.56 (5.80 (s, 1H), 5.98-6.05 (m, 1H), 6.59 (dd, J$_1$=15.5 Hz, J$_2$=1.8 Hz 1H) 7.17-7.30 (m, 6H), 7.77 (s, 1H).

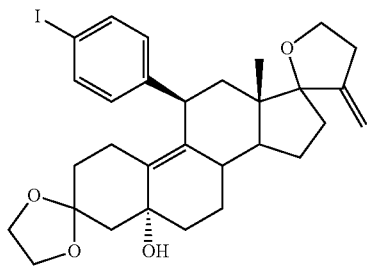 [SMILES: C=C1CCOC12CCC1C3CC[C@@]4(O)CC5(CCC4=C3[C@@H](c3ccc(I)cc3)C[C@@]12C)OCCO5]

3,3-Ethylenedioxy-5α-hydroxy-11β-(4'-[iodophenyl)-17,23-epoxy-19,24-dinor-17α-chola-9,20-diene (11)

A solution of 1,4-diiodobenzene (5.14 g, 15.6 mmol) in anhydrous THF (50 mL) was cooled to −10° C. as a 2 M solution of isopropyl magnesium chloride (7.8 mL, 15.6 mmol) was added dropwise over a period of 15 min. After stirring for 20 min, cuprous chloride (257 mg, 2.6 mmol) was added as a solid and the reaction mixture was stirred for 30 min. A solution of the epoxide 10 (2 g, 5.2 mmol) in 20 ml of THF was added dropwise and stirred for 2 h slowly warming to 10° C. Quenched with aqueous ammonium chloride solution (50 mL) and extracted with ethyl acetate (2×50 mL). The combined organic layer was washed further with water and brine, dried over sodium sulfate and evaporated in vacuo to afford crude product. The crude product was purified on a silica column eluting with 30% ethyl acetate in hexane to afford 2.81 g (92%) of 11 as an off white solid.

$^1$H NMR (δ, CDCl$_3$, 300 MHz) 0.58 (s, 3H), 3.74 (s, 4H), 3.81-3.94 (m, 4H), 4.13 (d, J=6.2 Hz, 1H), 4.85 (s, 1H), 5.13 (s, 1H), 5.77 (s, 1H), 6.91 (d, J=8.5 Hz, 2H), 7.58 (d, J=8.4 Hz, 2H).

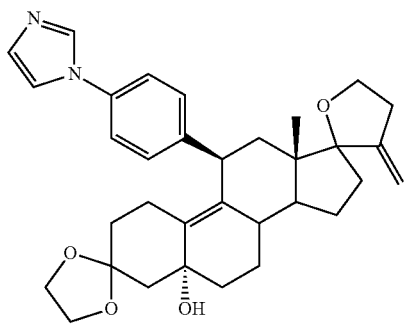 [SMILES: C=C1CCOC12CCC1C3CC[C@@]4(O)CC5(CCC4=C3[C@@H](c3ccc(-n4ccnc4)cc3)C[C@@]12C)OCCO5]

3,3-Ethylenedioxy-5α-hydroxy-11β-(4'-[1-imidazolyl)phenyl)-17,23-epoxy-19,24-dinor-17α-chola-9,20-diene (11)

A mixture of compound 11 (2.7 g, 4.6 mmol), imidazole (531 mg, 4.6 mmol), cuprous iodide (87 mg, 0.5 mmol), N, N-dimethyl glycine (94 mg, 0.9 mmol) and potassium carbonate (1.3 g, 9.2 mmol) in anhydrous DMSO (5 mL) was degassed three times applying vacuum and nitrogen and was immersed in to preheated oil bath at 110° C. The reaction mixture was heated for 60 h. After cooling to room temperature, the reaction mixture was diluted with ethyl acetate (100 mL) and filtered through a Celite pad. The filtrate was transferred to a separatory funnel and was washed with water, brine and dried over anhydrous sodium sulfate. The solvent was removed under vacuum to afford the crude product, which on purification by chromatography on SiO$_2$ column eluting with 10% acetone in ethyl acetate gave 2.4 g (98%) of required product 12 as a pale yellow amorphous solid.

$^1$H NMR (δ, CDCl$_3$, 300 MHz) 0.54 (s, 3H), 3.74-4.04 (m, 8H), 4.24 (d, J=6.8 Hz, 1H), 4.83 (s, 1H), 5.10 (s, 1H), 7.19 (s, 1H), 7.27-7.36 (m, 5H), 7.84 (s, 1H)

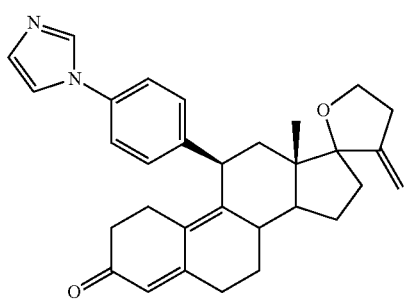 [SMILES: C=C1CCOC12CCC1C3CCC4=CC(=O)CCC4=C3[C@@H](c3ccc(-n4ccnc4)cc3)C[C@@]12C]

11β-(4'-[1-imidazolyl]phenyl)-17,23-epoxy-19,24-dinor-17α-chola-4,9,20-triene-3-one (Ie)

A solution of compound 12 (2.29 g, 4.33 mmol) in methanol (20 mL) was cooled to 0° C. as 5N hydrochloric acid (1.7 mL, 8.7 mmol) was added dropwise. The reaction mixture was stirred for 3 h warming to room temperature. Quenched by the careful addition of saturated sodium bicarbonate solution (30 mL) and extracted with ethyl acetate (2×50 mL). Combined organic layers were washed with water, brine and dried over anhydrous sodium sulfate. The solvent was removed in vacuo to obtain the crude product, which on purification by chromatography on SiO$_2$ column eluting with 10% acetone in dichloromethane gave 1.63 g (81%) of required compound Ie as a white solid.

$^1$H NMR (δ, CDCl$_3$, 300 MHz) 0.60 (s, 3H), 4.35 (d, J=7 Hz, 1H), 4.86 (s, 1H), 5.15 (s, 1H), 5.78 (s, 1H), 7.19 (s, 1H), 7.22-7.36 (m, 5H), 7.84 (s, 1H)

Example 1

Nuclear Receptor Profiling

Determination of the agonist/antagonist nature of the test compounds was carried out using Invitrogen's SelectScreen™ Cell-based nuclear receptor profiling service which uses the GeneBLAzer® Beta-lactamase reporter technology. Basically this assay uses a Beta-lactamase cDNA under transcriptional control of an Upstream Activator Sequence (UAS). The UAS is activated by the GAL4 transcription factor DNA binding domain (DBD), which is expressed as a fusion protein with the target receptor ligand binding domain (LBD). Upon ligand binding, the GAL4 (DBD)-NR(LDB) binds to the UAS, which controls transcription of Beta-lactamase. Beta-lactamase cleaves a special engineered fluorescent substrate which results in a change in the measured fluorescence wavelength.

The generalized protocol used for the Progesterone Antagonist Screen, activated by control Agonist R5020 is as follows:
The progesterone receptor-LBD-UAS-bla HEK 293T cells are thawed and prepared as described above for the Agonist screen. 4 µL of a 10× serial dilution of control antagonist RU486 (starting concentration, 100 nM) or test compounds are added to appropriate wells of a TC-Treated assay plate. 32 µL of cell suspension is added to the wells which is then pre-incubated at 37° C./5% CO2 in a humidified incubator with test compounds and control antagonist titration for 30 min. 4 µL of a 10× control agonist (see above) at the predetermined EC80 concentration is added to wells containing the control antagonist or test compounds. The plate is incubated for 16-24 h at 37° C./5% CO2 in a humidified incubator. 8 µL of 1 µM Substrate Loading Solution is added to each well and the plate is incubated for 2 h at room temperature. The plate is then read on a fluorescence plate reader (Tecan Safire).

The generalized protocol for the Glucocorticoid Antagonist Screen activated by control Agonist Dexamethasone was carried out as described for the Progesterone Antagonist Screen with the exception that glucocorticoid receptor-LBD-UAS-bla HEK 293T cells were used. The control antagonist used for the glucocorticoid assay was also RU486.

The results of these tests for the indicated test compounds are shown in Table I

| Compounds | Progesterone Antagonist (%) | Glucocorticoid Antagonist (%) |
| --- | --- | --- |
| ZK 230211 | 81 | 6 |
| Ia | 267 | 9 |
| Ib | 34 | 83 |
| Ic | 54 | 31 |
| Id | 90 | 13 |
| Ie | 163 | 5 |

Values are given in relative to RU486, which is 100%

Example 2

Pregnant guinea pig model as described by Walter Elger et. al J. Steroid Biochem Vol 25, No. 5B, pp 835-845, 1986:

Adult female guinea pigs weighing around 500 g were housed and tested for their cycle status by checking the vaginal opening every day.

Figure 2:
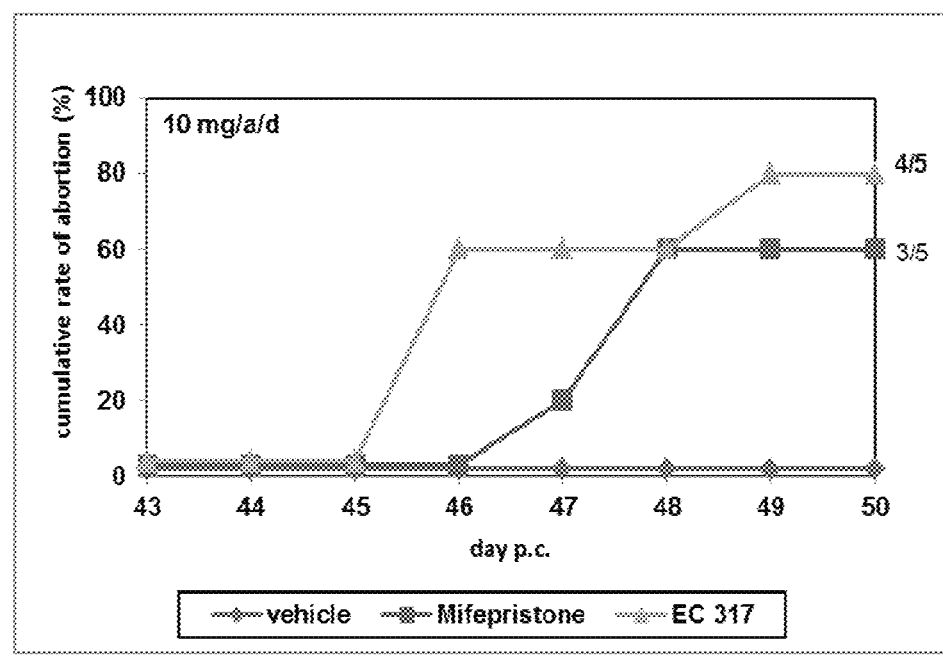
FIG. 2 is a graph of the cumulative rate of abortion when 10 mg/a/d of a compound of structure 1 is tested using the pregnant guinea pig model.

In the second cycle, three female animals will be cohoused with one male animal on day 15 after the first day the vaginal opening was detected. Day 16 of the cycle will be considered first day of pregnancy. The pregnant animals are randomized in the different treatment groups and will be treated on day 43 and 44 of the pregnancy with the test substances dissolved in 0.2 ml of benzyl benzoate/*ricinus* oils subcutaneously. Animals are checked for vaginal bleeding and number and timing of aborted foetii. FIG. 1 shows the test results for 3 mg/a/d, while FIG. 2 shows teat results for 10 mg/a/d.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:
1. A compound having the structure of formula (I):

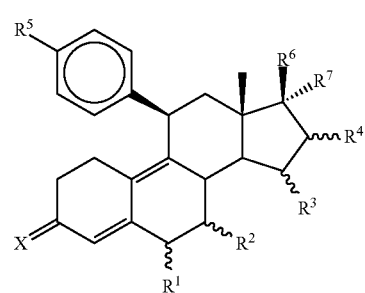

wherein:
X is O or H$_2$
R$^1$ is a hydrogen atom, a straight-chain C$_1$-C$_5$ alkyl group, a branched C$_3$-C$_5$ alkyl group, a C$_3$-C$_5$ cycloalkyl group or a halogen atom;
R$^2$ is a hydrogen atom, a straight-chain C$_1$-C$_5$ alkyl group, a branched C$_3$-C$_5$ alkyl group, a C$_3$-C$_5$ cycloalkyl group or a halogen atom; or
R$^1$ and R$^2$ together are a methylene group,
R$^3$ is a hydrogen atom, a straight-chain C$_1$-C$_5$ alkyl group, a branched C$_3$-C$_5$ alkyl group, a C$_3$-C$_5$ cycloalkyl group or a halogen atom;
R$^4$ is a hydrogen atom, a straight-chain C$_1$-C$_5$ alkyl group, a branched C$_3$-C$_5$ alkyl group, a C$_3$-C$_5$ cycloalkyl group or a halogen atom; or
R$^3$ and R$^4$ together are an additional bond or a methylene group,
R$^5$ an N imidazolyl group that is optionally substituted by one or more alkyl groups
R$^6$ stands for a free, etherified or esterified hydroxyl group, R⁷ stands for a radical of formula $C_nF_mH_o$ whereby n is 2, 3, 4, 5 or 6 with m≥1 and m+o=2n+1 or 2n−1 or 2n−3.

2. The compound of claim 1, wherein:
X is O;
R¹ and R² are hydrogen atoms;
R³ and R⁴ are hydrogen atoms
R⁵ is an N imidazolyl group;
R⁶ is a hydroxyl group,
R⁷ stands for a radical of formula $C_nF_mH_o$ whereby n is 2, 3, 4, 5 or 6 with m≥1 and m+o=2n+1 or 2n−1 or 2n−3.

3. The compound of claim 1, wherein:
X is O;
R¹ and R² together are a methylene group,
R³ and R⁴ together are an additional bond or a methylene group,
R⁵ is an N imidazolyl group;
R⁶ is a hydroxyl group,
R⁷ stands for a radical of formula $C_nF_mH_o$ whereby n is 2, 3, 4, 5 or 6 with m≥1 and m+o=2n+1 or 2n−1 or 2n−3.

4. The compound of claim 1, wherein:
X is O;
R¹ and R² are hydrogen atoms;
R³ and R⁴ are hydrogen atoms
R⁵ is an N imidazolyl group;
R⁶ is a hydroxyl group,
R⁷ stands for a radical of formula $C_nF_mH_o$ whereby n is 2, 3, 4, 5 or 6 with m≥1 and m+o=2n+1.

5. The compound of claim 1, wherein:
X is O;
R¹ and R² are hydrogen atoms;
R³ and R⁴ are hydrogen atoms
R⁵ is an N imidazolyl group;
R⁶ is a hydroxyl group,
R⁷ stands for a radical of formula $C_nF_mH_o$ whereby n is 2, 3, 4, 5 or 6 with m≥1 and m+o=2n−1.

6. The compound of claim 1, wherein:
X is O;
R¹ and R² are hydrogen atoms;
R³ and R⁴ are hydrogen atoms
R⁵ is an N imidazolyl group;
R⁶ is a hydroxyl group,
R⁷ stands for a radical of formula $C_nF_mH_o$ whereby n is 2, 3, 4, 5 or 6 with m≥1 and m+o=2n−3.

7. The compound of claim 1, wherein the compound has the structure:

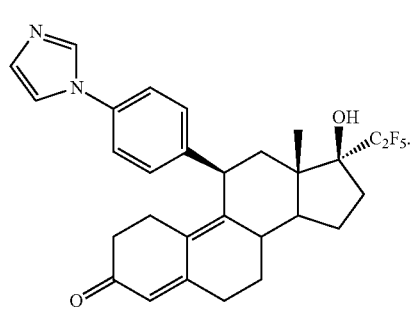

Ia

8. The compound of claim 1, wherein the compound has the structure:

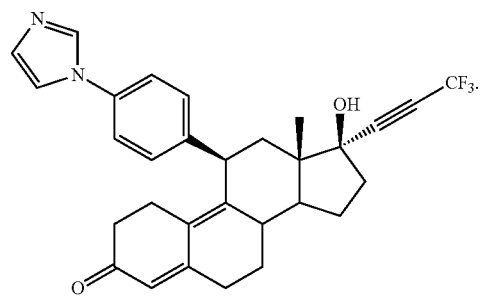

Ib

9. The compound of claim 1, wherein the compound has the structure:

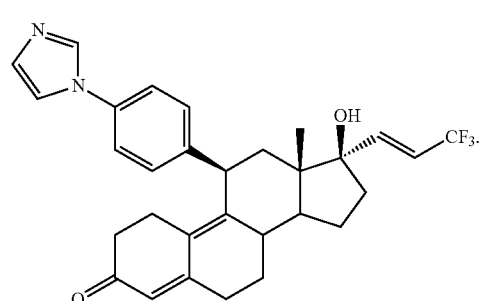

Ic

10. The compound of claim 1, wherein the compound has the structure:

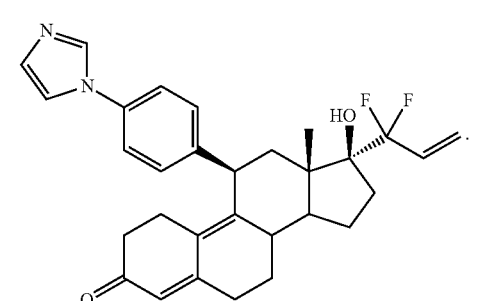

Id

11. A compound having the structure of formula (I):

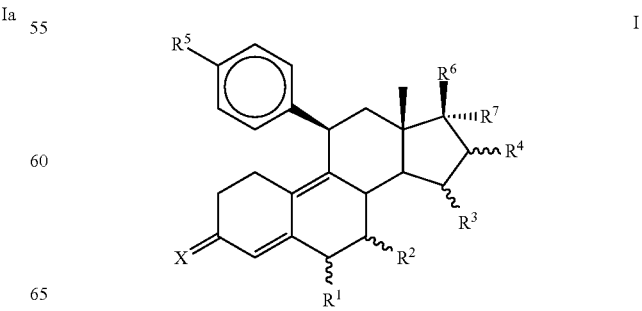

I wherein:

X is O or H$_2$

R$^1$ is a hydrogen atom, a straight-chain C$_1$-C$_5$ alkyl group, a branched C$_3$-C$_5$ alkyl group, a C$_3$-C$_5$ cycloalkyl group or a halogen atom;

R$^2$ is a hydrogen atom, a straight-chain C$_1$-C$_5$ alkyl group, a branched C$_3$-C$_5$ alkyl group, a C$_3$-C$_5$ cycloalkyl group or a halogen atom; or R$^1$ and R$^2$ together are a methylene group, R$^3$ is a hydrogen atom, a straight-chain C$_1$-C$_5$ alkyl group, a branched C$_3$-C$_5$ alkyl group, a C$_3$-C$_5$ cycloalkyl group or a halogen atom;

R$^4$ is a hydrogen atom, a straight-chain C$_1$-C$_5$ alkyl group, a branched C$_3$-C$_5$ alkyl group, a C$_3$-C$_5$ cycloalkyl group or a halogen atom; or R$^3$ and R$^4$ together are an additional bond or a methylene group;

R$^5$ an N imidazolyl group that is optionally substituted by one or more alkyl groups; and R$^6$ and R$^7$ are

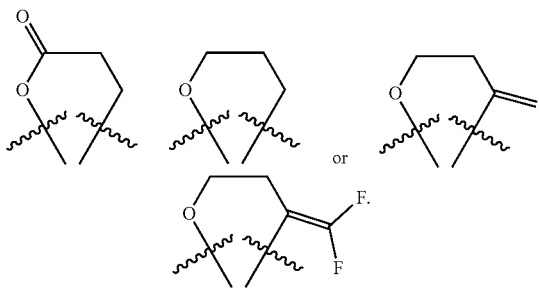

or

12. The compound of claim 11, wherein:

X is O

R$^1$ and R$^2$ are hydrogen atoms;

R$^3$ and R$^4$ are hydrogen atoms;

R$^5$ an N imidazolyl group that is optionally substituted by one or more alkyl groups; and R$^6$ and R$^7$ are

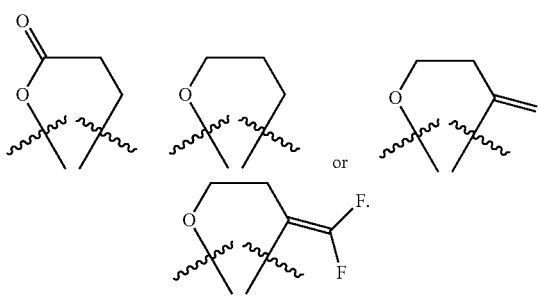

or

13. The compound of claim 11, wherein:

X is O

R$^1$ and R$^2$ together are a methylene group,

R$^3$ and R$^4$ together are an additional bond or a methylene group;

R$^5$ an N imidazolyl group that is optionally substituted by one or more alkyl groups; and R$^6$ and R$^7$ are

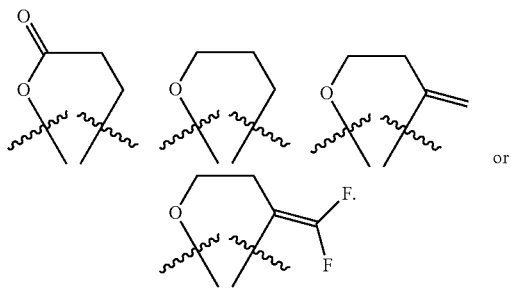

or

14. The compound of claim 11, wherein:

X is O

R$^1$ and R$^2$ are hydrogen atoms;

R$^3$ and R$^4$ are hydrogen atoms;

R$^5$ an N imidazolyl group that is optionally substituted by one or more alkyl groups; and R$^6$ and R$^7$ are

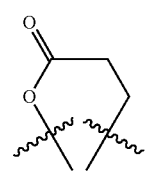

15. The compound of claim 11, wherein:

X is O

R$^1$ and R$^2$ are hydrogen atoms;

R$^3$ and R$^4$ are hydrogen atoms;

R$^5$ an N imidazolyl group that is optionally substituted by one or more alkyl groups; and R$^6$ and R$^7$ are

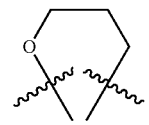

16. The compound of claim 11, wherein:

X is O

R$^1$ and R$^2$ are hydrogen atoms;

R$^3$ and R$^4$ are hydrogen atoms;

R$^5$ an N imidazolyl group that is optionally substituted by one or more alkyl groups; and R$^6$ and R$^7$ are

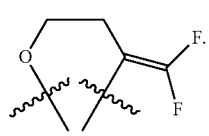 [SMILES: *OCCC(*)=C(F)F]

17. The compound of claim 11, wherein the compound has the structure:
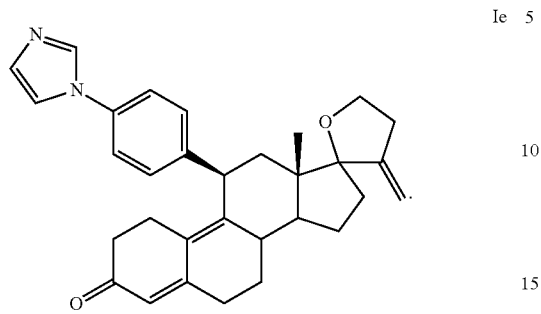
Ie
* * * * *